(12) United States Patent
Takeda

(10) Patent No.: US 7,672,707 B2
(45) Date of Patent: Mar. 2, 2010

(54) SENSOR FOR MAGNETOENCEPHALOGRAPHY METER AND SUPERMULTICHANNEL MAGNETOENCEPHALOGRAPHY METER SYSTEM USING THE SAME

(75) Inventor: Tsunehiro Takeda, Ibaraki (JP)

(73) Assignee: Japan Science and Technology Agency, Saitama (JP)

( * ) Notice: Subject to any disclaimer, the term of this patent is extended or adjusted under 35 U.S.C. 154(b) by 1320 days.

(21) Appl. No.: 10/516,106

(22) PCT Filed: Jun. 11, 2003

(86) PCT No.: PCT/JP03/07419

§ 371 (c)(1),
(2), (4) Date: Nov. 30, 2004

(87) PCT Pub. No.: WO2004/110269

PCT Pub. Date: Dec. 23, 2004

(65) Prior Publication Data

US 2005/0234328 A1    Oct. 20, 2005

(51) Int. Cl.
    *A61B 5/05*    (2006.01)
(52) U.S. Cl. .................. 600/409; 324/244; 324/260
(58) Field of Classification Search .......... 600/409; 324/244–261
    See application file for complete search history.

(56) References Cited

U.S. PATENT DOCUMENTS

| | | | | |
|---|---|---|---|---|
| 4,801,882 A | * | 1/1989 | Daalmans | 324/248 |
| 4,913,152 A | * | 4/1990 | Ko et al. | 600/409 |
| 4,982,157 A | * | 1/1991 | Seifert | 324/248 |
| 5,323,777 A | * | 6/1994 | Ahonen et al. | 600/409 |
| 5,444,373 A | * | 8/1995 | Johnson et al. | 324/248 |
| 5,986,280 A | * | 11/1999 | Kugai | 257/34 |
| 6,370,414 B1 | * | 4/2002 | Robinson | 600/409 |
| 6,665,552 B2 | * | 12/2003 | Yokosawa et al. | 600/409 |
| 6,665,553 B2 | * | 12/2003 | Kandori et al. | 600/409 |
| 2003/0141868 A1 | * | 7/2003 | Bakharev | 324/248 |
| 2004/0002645 A1 | * | 1/2004 | Ewing et al. | 600/409 |

FOREIGN PATENT DOCUMENTS

| | | | |
|---|---|---|---|
| EP | 481211 A2 | * | 4/1992 |
| JP | 02-116766 A | | 5/1990 |
| JP | 09-164123 A | | 6/1997 |
| JP | 09164123 A | * | 6/1997 |
| JP | 3566258 B2 | * | 9/2004 |

OTHER PUBLICATIONS

International Search Report mailed on Aug. 19, 2003.

* cited by examiner

*Primary Examiner*—Brian Casler
*Assistant Examiner*—Parikha S Mehta
(74) *Attorney, Agent, or Firm*—Rader, Fishman & Grauer, PLLC

(57) ABSTRACT

This invention relates to a super-multichannel MEG system comprising sensors produced by printing sensor coils on thin films in positions shifted from each other and by laminating multiple thin-film sensor coils together. Intended for use in a multichannel MEG system comprising a dewar, the sensors are arrayed in the dewar to detect biomagnetism and the Superconducting QUantum Interference Devices (SQUIDs) to detect signals coming from the sensors. These sensors are characterized by the sensor coils being printed on thin films in positions shifted from each other laterally and longitudinally and by their being laminated in the required number.

4 Claims, 3 Drawing Sheets

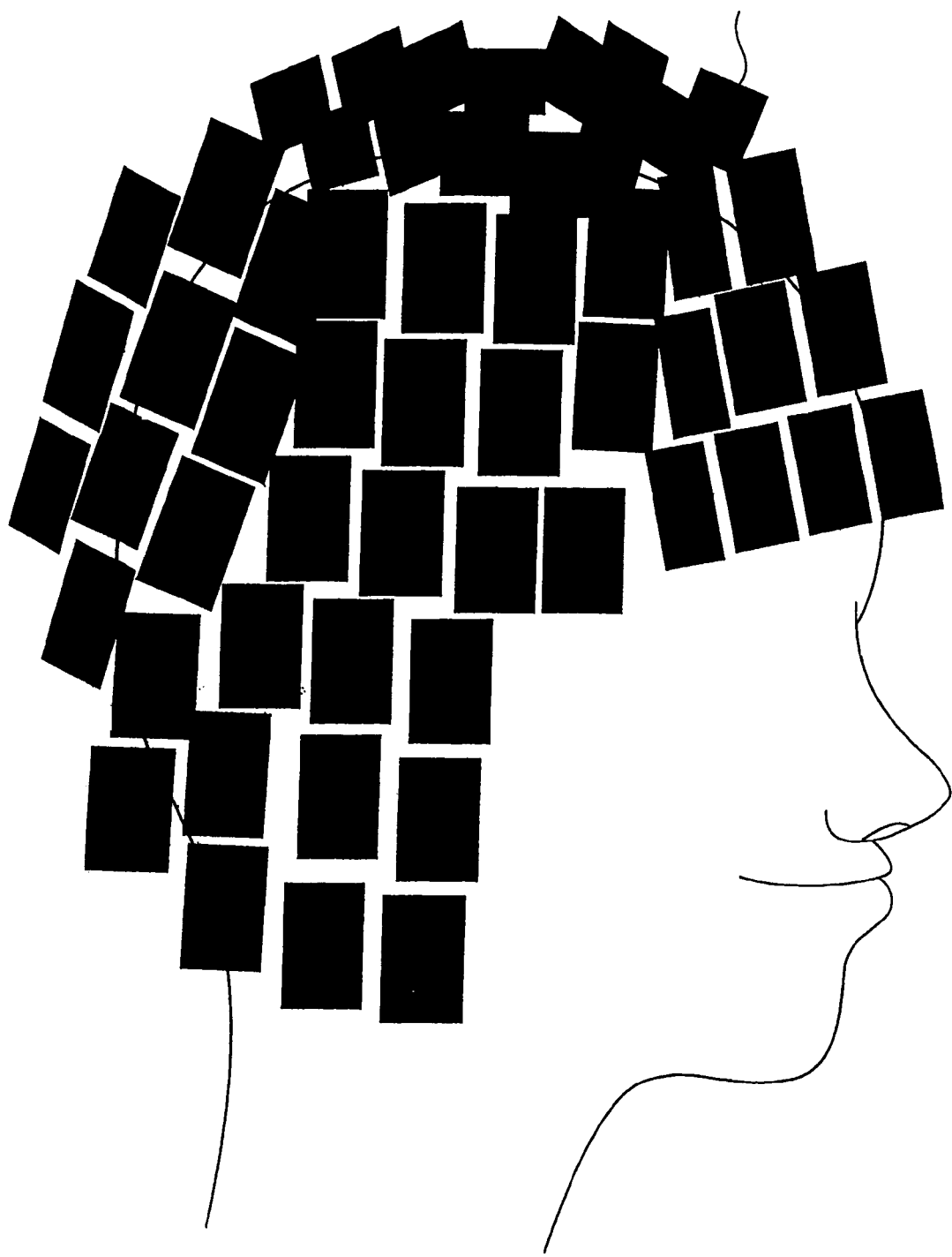

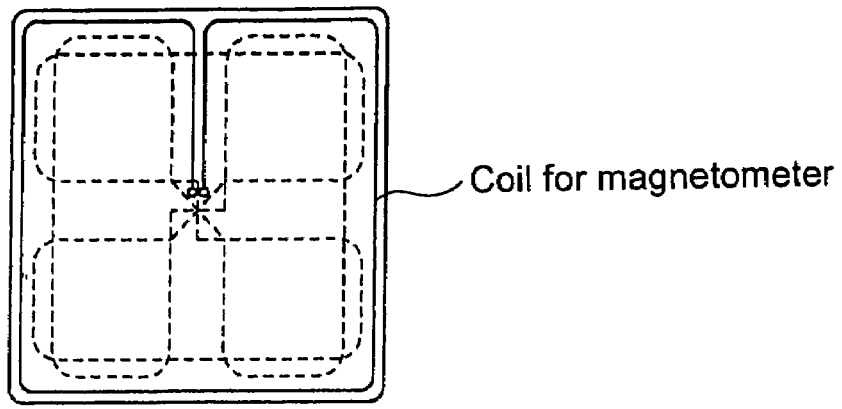
FIG. 3A — Coil for magnetometer
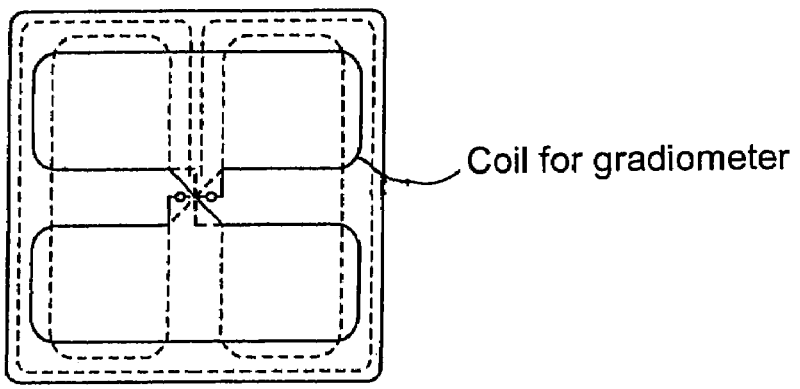
FIG. 3B — Coil for gradiometer
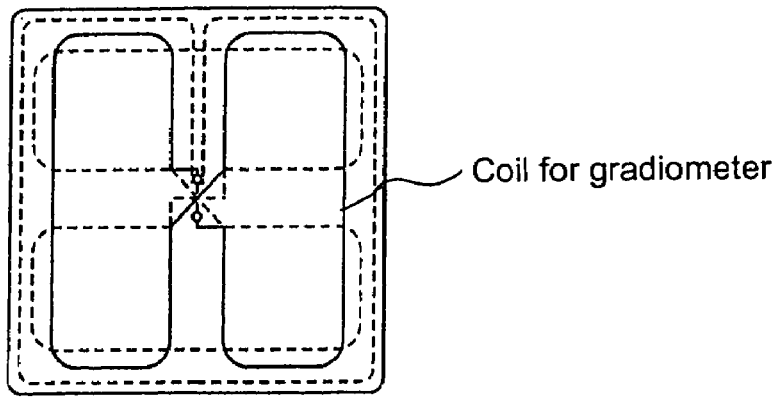
FIG. 3C — Coil for gradiometer

SENSOR FOR MAGNETOENCEPHALOGRAPHY METER AND SUPERMULTICHANNEL MAGNETOENCEPHALOGRAPHY METER SYSTEM USING THE SAME

TECHNICAL FIELD

This invention relates to a super-multichannel magnetoencephalography system used to take measurements of the magnetic fields generated in the brains of the subjects. Specifically, it relates to a super-multichannel magnetoencephalography system that is characterized by the structure of the sensors arrayed to surround the head of the subject.

BACKGROUND OF THE INVENTION

The human brain generates electric signals. These signals are very weak, but can be measured non-invasively by various methods. One of such method is the biomagnetism-measuring method which is used to measure the magnetic field on the outer surface of the head created by electric currents in the brain.

A magnetoencephalography (MEG) system (hereinafter referred to as the MEG system) is a specially improved, highly sensitive device for detecting magnetic fields, and comprises magnetic field sensors, detectors for the currents flowing through the sensors, and related electronic units. The MEG system has much potential as a non-invasive device for measuring brain functions because it has high time and space resolutions.

The magnetic field sensors of a planar type used in such a system typically comprise electric wires in the shape of multi-loop coils that create minute electric currents when they are penetrated by a magnetic flux. For example, as shown in FIG. 3, a sensor comprises a coil (a) for the magnetometer, and two directional derivative coils (b) and (c) for the gradiometer that detects the direction of magnetic field gradient. These three coils, (a), (b), and (c), are combined, overlaid, and integrated with each other to obtain a multi-layer laminate. Sensors, without coil (a) but comprising the coils (b) and (c) are in common use. Also, sensors using only the coil (a) are also available.

Each sensor coil is required to have a surface area of a few square centimeters for the coil to have enough sensitivity in the above-described system. If sensor coils requiring such an area were arrayed closely on the surface of the head, the number of coils would have to be limited, as shown in FIG. 2, with the upper limit being several hundreds of channels at the largest.

One objective of this invention is to create a super-multichannel MEG system capable of very high resolutions ranging from several hundreds to several tens of thousands of magnifications, with said system comprising sensors characterized by the sensor coils being printed on thin films in positions shifted from each other laterally and longitudinally by a length of $\{a\}/\{n\}$ and the sensor coils being laminated in a number of $\{n\}^2$ sheets where $\{a\}$ is the length of a side of the thin-film coil, and $\{n\}$ is a natural number, and wherein the signals coming from many corresponding thin-film sensors are sent in parallel with each other, and are switched over by the input unit of each multichannel-Superconducting QUantum Interference Device (SQUID).

Another objective of this invention is to create a super-multichannel MEG system capable of very high resolutions wherein the sensors are produced as described above by printing sensor coils on thin films in positions shifted from each other laterally and longitudinally by a length of a/n and laminating $\{n\}^2$ sheets of thin-film coils, and wherein a multiple number of such sensors are arrayed longitudinally and end-to-end, while aligning them accurately, to make it possible to detect the difference in electric currents generated by the corresponding coils and to measure the primary derivative or the high-order derivative in the axial direction of the magnetic field.

DISCLOSURE OF THE INVENTION

The means adopted by this invention to solve the above-described technical problem and to achieve the above-described objectives comprises the sensors, which are used in the magnetoencephalometer, according to claim 1, and are characterized by the sensor coils being printed on thin films in positions shifted from each other laterally and longitudinally and by the sensors being laminated in the required number of sheets.

Another means of implementing this invention comprises the sensors, which are used in the magnetoencephalometer and are characterized by the sensor coils being printed on thin films in positions shifted from each other laterally and longitudinally by a length of $\{a\}/\{n\}$, and by the sensors being laminated in a number of $\{a\}^2$ sheets where $\{a\}$ is the length of a side of the thin-film coil, and $\{n\}$ is a natural number.

Another means of implementing this invention comprises the sensors, which are used in the magnetoencephalometer and are characterized by the above-described sensors comprising laminated sensor coils being arrayed longitudinally and end-to-end, while aligning them accurately, to make it possible to detect the difference in electric currents generated by the corresponding coils and to measure the primary derivative or the high-order derivative in the axial direction of the magnetic field.

Another means of implementing this invention comprises a super-multichannel MEG system characterized by this system comprising the above-described sensors, high-speed switching means corresponding to each coil in the sensor, and SQUIDs arrayed correspondingly with the high-speed switching means.

BRIEF DESCRIPTION OF THE DRAWINGS

FIG. 2 is a schematic diagram showing the layout of sensors on the head.

FIGS. 3(a), 3(b) and 3(c) show some examples of sensor coils of the conventional planar type.

PREFERRED EMBODIMENT OF THE INVENTION

Figure 1:
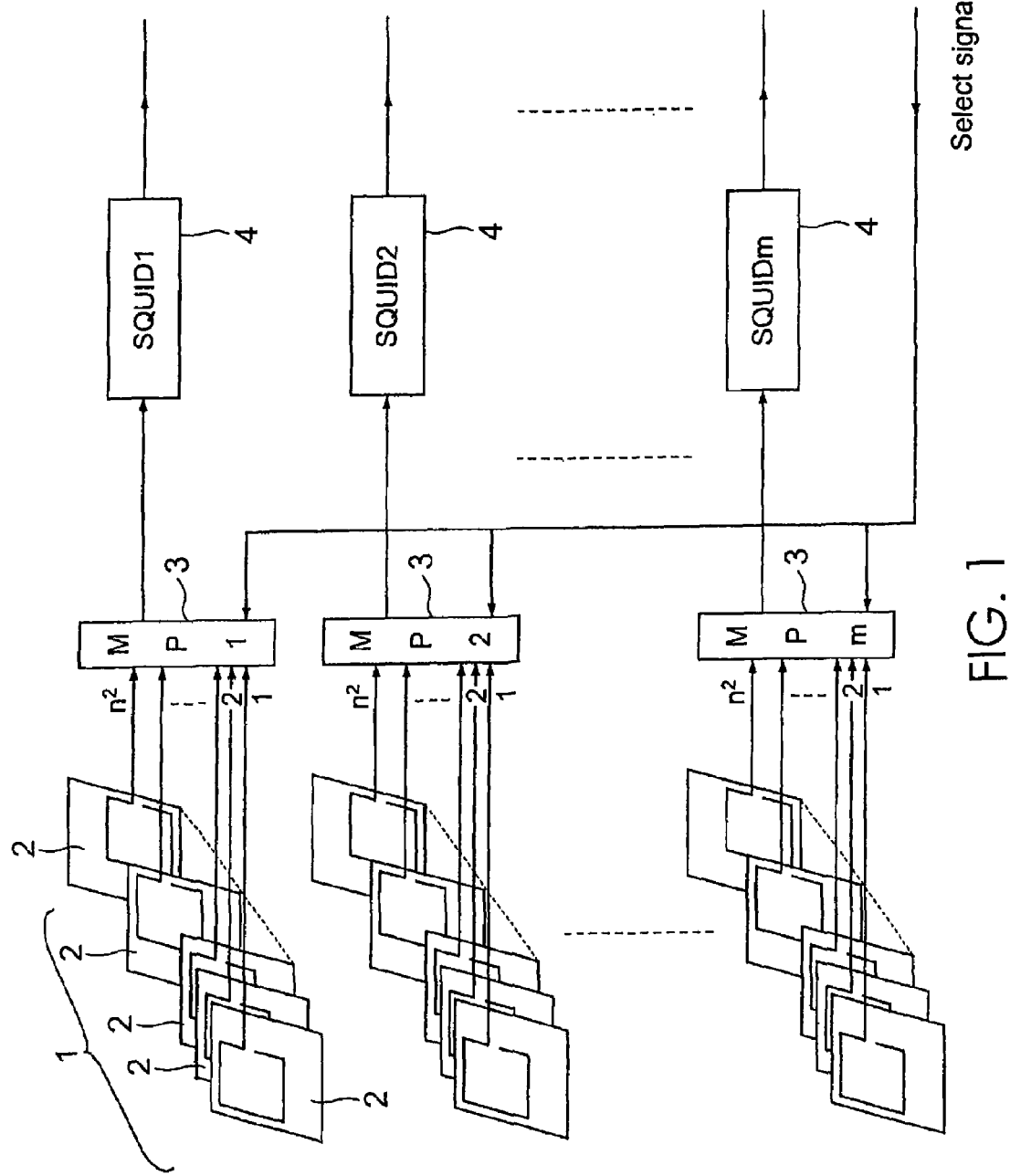
FIG. 1 is a diagram that explains the configuration of the sensors of this invention.

This invention is further described with respect to its preferred embodiment of the super-multichannel MEG system, while referring to the drawings in which FIG. 1 is an explanatory diagram showing the sensor coils used in this MEG system.

In FIG. 1, sensors 1 comprises thin-film coils having the same function as conventional sensor coils of the planar type, but the coils in this invention are printed in positions shifted in the lateral and longitudinal directions precisely by a length of $\{a\}/\{a\}$, and the sensor coils are laminated in the number of $\{n\}^2$, where $\{a\}$ is the length of a side of thin-film coil, and $\{n\}$ is a natural number. A coil printed on thin film has a thickness of several μm. Even if several hundreds to several thousands of coil sheets were laminated, the sensor would have a maximum thickness of only several millimeters. Precise lamination can be easily achieved using contemporary technology.

As shown in FIG. 2, a multiple number of the sensors 1 are arrayed on the head. The sensor coils 2 of each sensor 1 are connected to a corresponding SQUID 4, as in a conventional system, by way of a corresponding switching means 3, such as a multiplexer. Thus, when the multiplexer is switched over, one by one, from 1 to $\{n\}^2$, a measuring system having as many as several tens of thousands of magnifications can be configured, using the numbers of SQUIDs and amplifiers similar to those used in conventional technology. As regards the units downstream of the SQUIDs, a conventional system is used as is. These sensors are arrayed longitudinally, and the difference in electric currents generated by the corresponding coils is obtained to measure the primary derivative or the high-order derivative in the axial direction of the magnetic field. Thus, the gradiometer in the axial direction can be configured. In this manner, it is possible to set up a system capable of obtaining ultrahigh resolutions merely by using thin-film technology to multiplex the sensors while making use of a configuration similar to existing electronic systems.

A major aspect of a system having the above-described configuration is that a super-multichannel system can be built at a lower cost with no need to prepare large electronic circuits downstream of the SQUIDs. This can be done when the output from the i-th layer is switched by a high-speed switching means so that the output can be electronically combined at the same time at the multichannel SQUID. Since the signal components measured by the MEG meter are only several hundreds of Hz, this switching operation can be performed at a full speed, ensuring synchronized measurements.

With this system, the information detected by a sensor is determined by its number of laminated coils. In large laminates, the number of sensor coils increase with an increase in the number of laminated sheets even when there is no change in the number of sensors arrayed on the head. Information is collected in amounts much larger than the amounts collected by conventional sensor coils. Therefore, it is possible to set up a system having ultrahigh resolutions ranging from several hundreds to several tens of thousands of magnifications as compared to conventional systems.

The preferred embodiment of the sensors according to this invention has been described above. However, it is to be understood that the most feasible method and equipment have been explained simply to describe the embodiment of this invention. For example, the length of $\{a\}/\{n\}$ in which the sensors are shifted need not be always constant, and the lamination need not be in the number of $\{n\}^2$, because it is also possible to obtain the same result if the output data from the above laminated sensor coils are processed using adequate software. Furthermore, the planar type of sensor coil is not limited to the square shape, but the sensor coils may have other shapes. The above embodiment of this invention has been described for the sensors of the planar type. However, the conventional gradiometer or the high-order derivative sensors can also be configured by arraying multiple sensors longitudinally and end-to-end, while aligning the laminated sensors accurately. The sensors can be connected to the SQUIDs by way of the switching means to set up an MEG system. These sensors need not be placed on the head laterally, but may be placed vertically to measure the magnetic field components that are parallel to the head. An appropriate switching means of contemporary technology can be utilized for this invention.

Any other embodiments of this invention can be implemented without departing from the spirit of this invention and its major characteristics. Therefore, the above-described embodiment of this invention is merely for explanatory purposes in all respects and should not be construed as limiting.

INDUSTRIAL APPLICABILITY

Each of the sensors according to this invention comprises sensor coils that are printed on thin films in positions shifted from each other at certain lateral and longitudinal directions and are laminated together. The signals coming from multiple thin-film sensor coils are sent in parallel and switched over by the input units of the multichannel SQUIDs. By adopting such switching means, it is possible to obtain a high-resolution system that has resolutions ranging from several hundreds to several tens of thousands of magnifications, as compared with conventional systems.

What is claimed is:

1. A sensor unit for use in a magnetoencephalometer, the unit comprising:
   a plurality of sensor, each of which comprises a film and a sensor coil printed thereon, each of the sensor coils is arranged in a position shifted from one another laterally and longitudinally and is laminated in an overlapped manner,
   wherein each of the sensor coils senses signals at a different sensing position of an object to be measured,
   wherein said sensor coils are shifted in positions precisely by a length of $\{a\}/\{n\}$ in the lateral and longitudinal directions and are laminated together in the number of $\{n\}^2$, and
   wherein $\{a\}$ is the length of a side of the sensor coil, and $\{n\}$ is a natural number.

2. The sensor unit of claim 1,
   wherein the plurality of sensors are configured to detect the difference in electric currents generated by the corresponding sensor coils and to measure the primary derivative or the high-order derivative in the axial direction of the magnetic field.

3. The sensor unit of claim 2, further comprising:
   high-speed switching corresponding to each said sensor coil in the sensor, and
   superconducting quantum interference devices arranged to correspond with the high-speed switching.

4. The sensor unit of claim 1, further comprising:
   high-speed switching corresponding to each said sensor coil in the sensor, and
   superconducting quantum interference devices configured to correspond with the high-speed switching.

* * * * *